United States Patent
Jung et al.

(10) Patent No.: US 8,658,698 B2
(45) Date of Patent: Feb. 25, 2014

(54) INSECTICIDAL COMPOUNDS

(75) Inventors: Pierre Joseph Marcel Jung, Stein (CH); Antoine Daina, Geneva (CH); Christopher Richard Ayles Godfrey, Stein (CH); Peter Renold, Stein (CH); Peter Maienfisch, Stein (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 120 days.

(21) Appl. No.: 13/054,252

(22) PCT Filed: Jul. 8, 2009

(86) PCT No.: PCT/EP2009/004921
§ 371 (c)(1), (2), (4) Date: Jan. 14, 2011

(87) PCT Pub. No.: WO2010/006725
PCT Pub. Date: Jan. 21, 2010

(65) Prior Publication Data
US 2011/0118356 A1    May 19, 2011

(30) Foreign Application Priority Data
Jul. 16, 2008 (GB) .................................. 0813042.9

(51) Int. Cl.
| A01N 37/18 | (2006.01) |
| C07C 233/65 | (2006.01) |
| A01P 5/00 | (2006.01) |
| A01P 7/02 | (2006.01) |
| A01P 7/04 | (2006.01) |

(52) U.S. Cl.
USPC .......................................... 514/620; 564/156

(58) Field of Classification Search
None
See application file for complete search history.

(56) References Cited

FOREIGN PATENT DOCUMENTS
WO   2008074427   6/2008

OTHER PUBLICATIONS

Poon et al., Analogues of erectile dysfunction drugs: an under-recognised threat, Hong Kong Med. J., Vol13, No. 5, Oct. 2007, p. 359.*
Wermuth, Similarity in Drugs: reflections on analogue design, Drug Discovery Today, vol. 11, No. 7/8, Apr. 2006, p. 349.*

* cited by examiner

Primary Examiner — Ernst Arnold
Assistant Examiner — Jianfeng Song
(74) Attorney, Agent, or Firm — R. Kody Jones

(57) ABSTRACT

A compound of formula (I) wherein $A^1$, $A^2$, $A^3$, $A^4$, $G^1$, $G^2$, $R^1$, $R^2$, L, $Q^1$, and $Q^2$ are as defined in claim 1; or a salt or N-oxide thereof. Furthermore, the present invention relates to processes and intermediates for preparing compounds of formula (I), to insecticidal, acaricidal, molluscicidal and nematicidal compositions comprising them and to methods of using them to combat and control insect, acarine, mollusc and nematode pests.

(I)

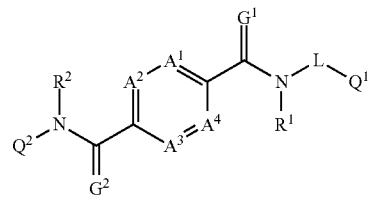

7 Claims, No Drawings

INSECTICIDAL COMPOUNDS

This application is a 371 of International Application No. PCT/EP2009/004921 filed Jul. 8, 2009, which claims priority to GB 0813042.9 filed Jul. 16, 2008, the contents of which are incorporated herein by reference.

The present invention relates to certain aromatic bisamide derivatives, to processes and intermediates for preparing them, to insecticidal, acaricidal, nematicidal and molluscicidal compositions comprising them and to methods of using them to combat and control insect, acarine, nematode and mollusc pests.

Certain aromatic bisamide derivatives were disclosed inter alia as insecticides in JP 61/291,575. Certain aromatic bisamide derivatives were disclosed inter alia as chemosterilants for insects in U.S. Pat. No. 3,720,712.

It has now surprisingly been found that certain aromatic bisamide derivatives have insecticidal properties.

The present invention therefore provides a compound of formula (I):

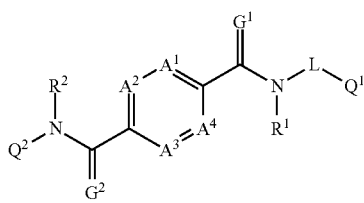

(I)

wherein
$A^1$, $A^2$, $A^3$ and $A^4$ are independently of each other C—H, C—$R^3$, or nitrogen;
$G^1$ and $G^2$ are independently of each other oxygen or sulfur;
$R^1$ is hydrogen, $C_1$-$C_8$alkyl, $C_1$-$C_8$alkylcarbonyl-, or $C_1$-$C_8$alkoxycarbonyl-;
$R^2$ is hydrogen, $C_1$-$C_8$alkyl, $C_1$-$C_8$alkylcarbonyl-, or $C_1$-$C_8$alkoxycarbonyl-;
each $R^3$ is independently halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkylcarbonyl-, or $C_1$-$C_8$alkoxycarbonyl-;
L is a single bond, or $C_1$-$C_6$alkylene;
$Q^1$ is $C_1$-$C_8$alkyl or $C_1$-$C_8$alkyl substituted by one to five $R^4$; or
$Q^1$ is $C_3$-$C_{10}$cycloalkyl or $C_3$-$C_{10}$cycloalkyl substituted by one to five $R^5$, or $C_3$-$C_{10}$cycloalkenyl or $C_3$-$C_{10}$cycloalkenyl substituted by one to five $R^5$, or
$Q^1$ is aryl or aryl substituted by one to five $R^6$, heterocyclyl or heterocyclyl substituted by one to five $R^6$, aryloxy or aryloxy substituted by one to five $R^6$, or heterocyclyloxy or heterocyclyloxy substituted by one to five $R^6$;
each $R^4$ is independently halogen, hydroxy, $C_1$-$C_8$alkoxy, N—$C_1$-$C_8$alkylamino-, N,N-di-($C_1$-$C_8$alkyl)amino-, N—$C_1$-$C_8$alkylcarbonylamino-, or (HOSO$_2$)S—;
each $R^5$ is independently halogen, hydroxy, $C_1$-$C_8$alkyl, or $C_1$-$C_8$alkoxycarbonyl-;
each $R^6$ is independently halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, N—$C_1$-$C_8$alkylamino-, N,N-di-($C_1$-$C_8$alkyl)amino-, N—$C_1$-$C_8$alkylcarbonylamino-, aryl or aryl substituted by one to five $R^7$, heterocyclyl or heterocyclyl substituted by one to five $R^7$, aryl-$C_1$-$C_4$alkyl- or aryl-$C_1$-$C_4$alkyl- wherein the aryl moitey is substituted by one to five $R^7$, heterocyclyl-$C_1$-$C_4$alkyl- or heterocyclyl-$C_1$-$C_4$alkyl- wherein the heterocyclyl moitiey is substituted by one to five $R^7$, aryloxy or aryloxy substituted by one to five $R^7$, or heterocyclyloxy or heterocyclyloxy substituted by one to five $R^7$;
each $R^7$ is independently halogen, cyano, nitro, $C_1$-$C_8$alkyl, $C_1$-$C_8$haloalkyl, $C_1$-$C_8$alkoxy, or $C_1$-$C_8$haloalkoxy; and
$Q^2$ is a moiety of formula (II) or (III)

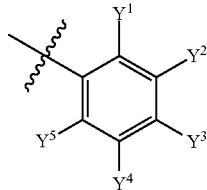

(II)

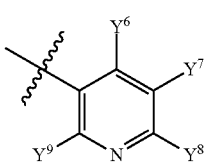

(III)

wherein
$Y^1$ and $Y^5$ are independently of each other halogen, cyano, $C_1$-$C_8$alkyl, $C_1$-$C_8$haloalkyl, $C_1$-$C_4$alkoxy-$C_1$-$C_4$-alkyl-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
$Y^3$ is $C_2$-$C_8$perfluoroalkyl, $C_1$-$C_8$ perfluoroalkylthio-, $C_1$-$C_8$perfluoroalkylsulfinyl-, or $C_1$-$C_8$perfluoroalkylsulfonyl-;
$Y^2$ and $Y^4$ are independently of each other hydrogen, halogen, or $C_1$-$C_8$alkyl;
$Y^6$ and $Y^9$ are independently of each other halogen, cyano, $C_1$-$C_8$alkyl, $C_1$-$C_8$haloalkyl, $C_1$-$C_4$alkoxy-$C_1$-$C_4$-alkyl-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
$Y^8$ is $C_2$-$C_8$perfluoroalkyl, $C_1$-$C_8$ perfluoroalkylthio-, $C_1$-$C_8$perfluoroalkylsulfinyl-, or $C_1$-$C_8$ perfluoroalkylsulfonyl-;
$Y^7$ is hydrogen, halogen, or $C_1$-$C_8$alkyl; or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkylcarbonyl, alkoxycarbonyl, alkylaminocarbonyl, dialkylaminocarbonyl) is a straight or branched chain and is, for example, methyl, ethyl, n-propyl, prop-2-yl, n-butyl, but-2-yl, 2-methyl-prop-1-yl or 2-methyl-prop-2-yl. The alkyl groups are preferably $C_1$ to $C_6$ alkyl groups, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Each alkylene moiety is a straight or branched chain and is, for example, —CH$_2$—, —CH$_2$—CH$_2$—, —CH(CH$_3$)—, —CH$_2$—CH$_2$—CH$_2$—, —CH(CH$_3$)—CH$_2$—, or —CH ($CH_2CH_3$)—. The alkylene groups are preferably $C_1$ to $C_3$ alkylene groups, more preferably $C_1$-$C_2$, most preferably $C_1$ alkylene groups.

Alkenyl moieties can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups.

Halogen is fluorine, chlorine, bromine or iodine.

Haloalkyl groups (either alone or as part of a larger group, such as haloalkoxy or haloalkylthio) are alkyl groups which are substituted by one or more of the same or different halogen atoms and are, for example, difluoromethyl, trifluoromethyl, chlorodifluoromethyl, 2,2,2-trifluoro-ethyl, or 3,3,3-trifluoro-propyl. Perfluoroalkyl groups (either alone or as part of a larger group, such as perfluoroalkylthio) are a particular type of haloalkyl group; they are alkyl groups which are completely substituted with fluorine atoms and are, for example, trifluoromethyl, pentafluoroethyl, heptafluoro-prop-2-yl, or nonafluoro-but-2-yl.

Cycloalkyl groups can be in mono- or bi-cyclic form. The cycloalkyl groups preferably contain 3 to 8 carbon atoms, more preferably 3 to 6 carbon atoms. Examples of monocyclic cycloalkyl groups are cyclopropyl, cyclobutyl, and cyclohexyl. An example of a bicyclic cycloalkyl group is bicyclo[2.2.1]heptan-2-yl. Where a cycloalkyl moiety is said to be substituted, the cycloalkyl moiety is preferably substituted by one to four substituents, most preferably by one to three substituents.

Cycloalkenyl groups can be in mono- or bi-cyclic form. The cycloalkenyl groups preferably contain 3 to 8 carbon atoms, more preferably 3 to 6 carbon atoms. An example of a monocyclic cycloalkenyl group is cyclohexenyl. Where a cycloalkenyl moiety is said to be substituted, the cycloalkenyl moiety is preferably substituted by one to four substituents, most preferably by one to three substituents.

In the context of the present specification the term "aryl" refers to a ring system which may be mono-, bi- or tricyclic. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

The term "heteroaryl" refers to an aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl. Examples of bicyclic groups include quinolinyl, cinnolinyl, quinoxalinyl, indolyl, indazolyl, benzimidazolyl, benzothiophenyl and benzothiazolyl. Other examples of bicyclic groups include purinyl

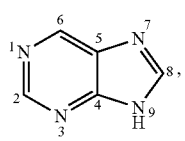

and 2H-pyrazolo[3,4-b]pyridyl

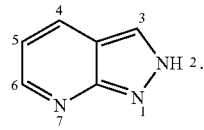

Preferred heteroaryl groups are pyridyl, pyrazolyl, thiophenyl, thiazolyl, quinolinyl, indolyl, and purinyl, pyridyl being most preferred. Where a heteroaryl moiety is said to be substituted, the heteroaryl moiety is preferably substituted by one to four substituents, most preferably by one to three substituents.

The term "heterocyclyl" is defined to include heteroaryl and in addition their unsaturated or partially unsaturated analogues. Examples of monocyclic groups include thietanyl, pyrrolidinyl, tetrahydro-furanyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,3]dioxolanyl, and 2,3-dihydro-benzo[1,4]dioxinyl. Preferred heterocyclyl groups are pyridyl, pyrazolyl, thiophenyl, thiazolyl, quinolinyl, indolyl, purinyl, piperidinyl, morpholinyl, tetrahydro-furanyl, [1,3]dioxolanyl, benzo[1,3]dioxolanyl, and 2,3-dihydro-benzo[1,4]dioxinyl. Where a heterocyclyl moiety is said to be substituted, the heterocyclyl moiety is preferably substituted by one to four substituents, most preferably by one to three substituents.

Preferred values of $A^1$, $A^2$, $A^3$, $A^4$, $G^1$, $G^2$, $R^1$, $R^2$, $R^3$, L, $Q^1$, $R^4$, $R^5$, $R^6$, $R^7$, $Q^2$, $Y^1$, $Y^2$, $Y^3$, $Y^4$, $Y^5$, $Y^6$, $Y^7$, $Y^8$, and $Y^9$ are, in any combination, as set out below.

Preferably no more than two of $A^1$, $A^2$, $A^3$ and $A^4$ are nitrogen.

Preferably $A^1$ is C—H or C—$R^3$, most preferably $A^1$ is C—$R^3$.

Preferably $A^2$ is C—H or C—$R^3$, most preferably $A^2$ is C—H.

Preferably $A^3$ is C—H or C—$R^3$, most preferably $A^3$ is C—H.

Preferably $A^4$ is C—H or C—$R^3$, most preferably $A^4$ is C—H.

Preferably $G^1$ is oxygen.
Preferably $G^2$ is oxygen.
Preferably $R^1$ is hydrogen, methyl, ethyl, methylcarbonyl-, or methoxycarbonyl-, more preferably hydrogen, methyl, or ethyl, even more preferably hydrogen, or methyl, most preferably hydrogen.

Preferably $R^2$ is hydrogen, methyl, ethyl, methylcarbonyl-, or methoxycarbonyl-, more preferably hydrogen, methyl, or ethyl, even more preferably hydrogen, or methyl, most preferably hydrogen.

Preferably each $R^3$ is independently halogen, cyano, nitro, $C_1$-$C_8$alkyl, or $C_1$-$C_8$haloalkyl, more preferably halogen or $C_1$-$C_8$alkyl, even more preferably $C_1$-$C_8$alkyl, most preferably methyl.

Preferably L is a single bond, —$CH_2$—, —$CH_2$—$CH_2$—, —$CH(CH_3)$—, or —$CH_2$—$CH_2$—$CH_2$—, more preferably single bond, —$CH_2$—, or —$CH_2$—$CH_2$—, even more preferably single bond, or —$CH_2$—, most preferably —$CH_2$—.

In a preferred embodiment $Q^1$ is $C_1$-$C_8$alkyl or $C_1$-$C_8$alkyl substituted by one to five $R^4$, preferably n-propyl or n-butyl, or n-propyl or n-butyl substituted by one to five $R^4$, most preferably n-propyl or n-propyl substituted by one to five $R^4$.

In a preferred embodiment $Q^1$ is $C_3$-$C_{10}$cycloalkyl or $C_3$-$C_{10}$cycloalkyl substituted by one to five $R^5$, or $C_3$-$C_{10}$cycloalkenyl or $C_3$-$C_{10}$cycloalkenyl substituted by one to five $R^5$, more preferably $C_3$-$C_{10}$cycloalkyl or $C_3$-$C_{10}$cycloalkyl substituted by one to five $R^5$, most preferably cyclohexyl or cyclohexyl substituted by one to five $R^5$.

In a preferred embodiment $Q^1$ is aryl or aryl substituted by one to five $R^6$, heterocyclyl or heterocyclyl substituted by one to five $R^6$, aryloxy or aryloxy substituted by one to five $R^6$, or heterocyclyloxy or heterocyclyloxy substituted by one to five $R^6$, most preferably $Q^1$ is aryl or aryl substituted by one to five $R^6$, heterocyclyl or heterocyclyl substituted by one to five $R^6$ (wherein the heterocyclyl is pyridyl, imidazolyl, furanyl, isoxazolyl, thiophenyl, thiazolyl, thiadiazolyl, quinolinyl, indolyl, indazolyl, benzimidazolyl, benzothiazolyl, purinyl, pyrrolidinyl, tetrahydro-furanyl, [1,3]dioxolanyl, piperazinyl, morpholinyl, benzo[1,3]dioxolanyl, 2,3-dihydro-benzofuranyl, or 2,3-dihydro-benzo[1,4]dioxinyl), or aryloxy or aryloxy substituted by one to five $R^6$.

In a preferred embodiment $Q^1$-L- is aryl or aryl substituted by one to five $R^6$, or heterocyclyl- or heterocyclyl-substituted by one to five $R^6$, more preferably $Q^1$-L- is aryl or aryl substituted by one to five $R^6$, or heteroaryl- or heteroaryl-substituted by one to five $R^6$ (wherein the heteroaryl is thiazolyl, quinolinyl, or purinyl).

In a preferred embodiment $Q^1$-L- is aryl-$C_1$-$C_4$alkyl- or aryl-$C_1$-$C_4$alkyl- wherein the aryl moiety is substituted by one to five $R^6$, or heterocyclyl-$C_1$-$C_4$alkyl- or heterocyclyl-$C_1$-$C_4$alkyl- wherein the heterocyclyl moiety is substituted by one to five $R^6$, more preferably $Q^1$ is aryl-$CH_2$— or aryl-$CH_2$— wherein the aryl moiety is substituted by one to five $R^6$, heterocyclyl-$CH_2$— or heterocyclyl-$CH_2$— wherein the heterocyclyl moiety is substituted by one to five $R^6$ (wherein the heterocyclyl is pyridyl, tetrahydro-furanyl, benzo[1,3]dioxolanyl, or 2,3-dihydro-benzo[1,4]dioxinyl), aryl-$CH_2$—$CH_2$— or aryl-$CH_2$—$CH_2$— wherein the aryl moiety is substituted by one to five $R^6$, or heterocyclyl-$CH_2$—$CH_2$— or heterocyclyl-$CH_2$—$CH_2$— wherein the heterocyclyl moiety is substituted by one to five $R^6$ (wherein the heterocyclyl is thiophenyl, indolyl, morpholinyl, or [1,3]dioxolanyl). It is particularly preferred when Q'-L- is pyridyl-$CH_2$—, in particular pyrid-2-yl-$CH_2$—.

Preferably each $R^4$ is independently halogen, hydroxy, $C_1$-$C_8$alkoxy, N—$C_1$-$C_8$alkylcarbonylamino-, or (HOSO$_2$—S)—, more preferably halogen, hydroxy, or $C_1$-$C_8$alkoxy, even more preferably chloro, fluoro, hydroxy, or methoxy, most preferably fluoro.

Preferably each $R^5$ is independently halogen, hydroxy, or $C_1$-$C_8$alkyl, more preferably hydroxy, or methyl, most preferably hydroxy.

Preferably each $R^6$ is independently halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkylthio-, $C_1$-$C_8$alkylsulfinyl-, $C_1$-$C_8$alkylsulfonyl-, N,N-dimethylamino-, $C_1$-$C_8$alkylcarbonyl-, $C_1$-$C_8$alkoxycarbonyl-, aryl or aryl substituted by one to five $R^7$, or heterocyclyl or heterocyclyl substituted by one to five $R^7$, more preferably bromo, chloro, fluoro, cyano, nitro, methyl, trifluoromethyl, methoxy, trifluoromethoxy, methylthio-, methylsulfinyl-, methylsulfonyl-, N,N-dimethylamino-, phenyl, pyrazolyl, or piperidinyl, most preferably chloro, fluoro, cyano, nitro, methyl, trifluoromethyl, methoxy, or trifluoromethoxy.

Preferably each $R^7$ is independently halogen, cyano, nitro, $C_1$-$C_8$alkyl, $C_1$-$C_8$haloalkyl, $C_1$-$C_8$alkoxy, or $C_1$-$C_8$haloalkoxy, most preferably chloro, fluoro, cyano, nitro, methyl, trifluoromethyl, methoxy, or trifluoromethoxy.

Preferably $Q^2$ is a moiety of formula (II).
Preferably $Y^1$ is halogen, cyano, methyl, ethyl, trifluoromethyl, or methoxymethyl, more preferably bromo, chloro, methyl, ethyl, methoxymethyl, most preferably bromo, chloro, methyl, ethyl.

Preferably $Y^2$ is hydrogen, chloro, fluoro, or methyl, most preferably hydrogen.

Preferably $Y^3$ is heptafluoro-propyl, heptafluoro-prop-2-yl, heptafluoro-propylthio-, heptafluoro-propylsulfinyl-, heptafluoro-propylsulfonyl-, heptafluoro-prop-2-ylthio-, heptafluoro-prop-2-ylsulfinyl-, heptafluoro-prop-2-ylsulfonyl-, or nonafluoro-but-2-yl.

In one embodiment $Y^3$ is $C_2$-$C_6$ perfluoroalkyl, most preferably $Y^3$ is heptafluoro-prop-2-yl or nonafluoro-but-2-yl.

Preferably $Y^4$ is hydrogen, chloro, fluoro, or methyl, most preferably hydrogen.

Preferably $Y^5$ is halogen, cyano, methyl, ethyl, or trifluoromethyl, most preferably bromo, chloro, methyl, or ethyl.

Preferably $Y^6$ is halogen, cyano, methyl, ethyl, trifluoromethyl, or methoxymethyl, more preferably bromo, chloro, methyl, ethyl, or methoxymethyl, most preferably bromo, chloro, methyl, or ethyl.

Preferably $Y^7$ is hydrogen, chloro, fluoro, or methyl, most preferably hydrogen.

Preferably $Y^8$ is heptafluoro-propyl, heptafluoro-prop-2-yl, heptafluoro-propylthio-, heptafluoro-propylsulfinyl-, heptafluoro-propylsulfonyl-, heptafluoro-prop-2-ylthio-, heptafluoro-prop-2-ylsulfinyl-, heptafluoro-prop-2-ylsulfonyl-, or nonafluoro-but-2-yl.

In one embodiment $Y^8$ is $C_2$-$C_6$ perfluoroalkyl, most preferably $Y^8$ is heptafluoro-prop-2-yl or nonafluoro-but-2-yl.

Preferably $Y^9$ is halogen, cyano, methyl, ethyl, trifluoromethyl, or methoxymethyl, more preferably bromo, chloro, methyl, ethyl, or methoxymethyl, most preferably bromo, chloro, methyl, or ethyl.

In a preferred embodiment $Q^2$ is 2-ethyl-6-methyl-4-(heptafluoro-prop-2-yl)-phenyl.

In a preferred embodiment $Q^2$ is 2-bromo-6-methyl-4-(heptafluoro-prop-2-yl)-phenyl.

In a preferred embodiment $Q^2$ is 2-bromo-6-ethyl-4-(heptafluoro-prop-2-yl)-phenyl.

In a preferred embodiment $Q^2$ is 2,6-dichloro-4-(heptafluoro-prop-2-yl)-phenyl.

In a preferred embodiment $Q^2$ is 2,6-dibromo-4-(heptafluoro-prop-2-yl)-phenyl.

In a preferred embodiment $Q^2$ is 2-bromo-6-chloro-4-(heptafluoro-prop-2-yl)-phenyl.

In a preferred embodiment $Q^2$ is 2-ethyl-6-methyl-4-(nonafluoro-but-2-yl)-phenyl.

In a preferred embodiment $Q^2$ is 2-bromo-6-methyl-4-(nonafluoro-but-2-yl)-phenyl.

In a preferred embodiment $Q^2$ is 2-bromo-6-ethyl-4-(nonafluoro-but-2-yl)-phenyl.

In a preferred embodiment $Q^2$ is 2,6-dichloro-4-(nonafluoro-but-2-yl)-phenyl.

In a preferred embodiment $Q^2$ is 2,6-dibromo-4-(nonafluoro-but-2-yl)-phenyl.

In a preferred embodiment $Q^2$ is 2-bromo-6-chloro-4-(nonafluoro-but-2-yl)-phenyl.

A preferred embodiment are compounds of formula (Ia) wherein $A^1$ is C-Me, $A^2$, $A^3$, $A^4$ are CH, and G', $G^2$, $R^1$, $R^2$, $Q^1$, L, and $Q^2$ are defined for a compound of formula (I). The preferences for $G^1$, $G^2$, $R^1$, $R^2$, $Q^1$, L, and $Q^2$ are the same as those defined for a compound of formula (I).

Certain intermediates are novel and as such form a further aspect of the invention. One group of novel intermediates are compounds of formula (VIII)

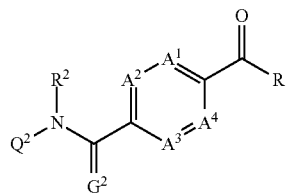

(VIII)

wherein $A^1$, $A^2$, $A^3$, $A^4$, $G^2$, $R^2$, and $Q^2$ are as defined for a compound of formula (I), and R is halogen, hydroxy, or $C_1$-$C_8$alkoxy; or a salt or N-oxide thereof. The preferences for $A^1$, $A^2$, $A^3$, $A^4$, $G^2$, $R^2$, and $Q^2$ are the same as the preferences set out for the corresponding substituents of a compound of formula (I). Preferably R is chloro, or hydroxy.

Another group of novel intermediates are compounds of formula (IX)

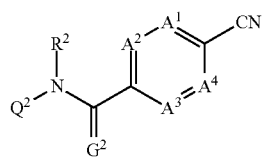

(IX)

wherein $A^1$, $A^2$, $A^3$, $A^4$, $G^2$, $R^2$, and $Q^2$ are as defined for a compound of formula (I); or a salt or N-oxide thereof. The preferences for $A^1$, $A^2$, $A^3$, $A^4$, $G^2$, $R^2$, and $Q^2$ are the same as the preferences set out for the corresponding substituents of a compound of formula (I).

The compounds in Tables 1 to 12 below illustrate the compounds of the invention.

TABLE 1

Table 1 provides 30 compounds of formula (Ia) wherein $G^1$ and $G^2$ are both oxygen, $R^1$ and $R^2$ are both hydrogen, $Q^2$ is 2-ethyl-6-methyl-4-(heptafluoro-prop-2-yl)-phenyl, and $Q^1$, and L have the values listed in the table below.

(Ia)

| Comp No. | $Q^1$ | L |
|---|---|---|
| 1.01 | phenyl- | —CH$_2$— |
| 1.02 | 4-chloro-phenyl- | —CH$_2$— |
| 1.03 | pyrid-2-yl- | —CH$_2$— |
| 1.04 | pyrid-3-yl- | —CH$_2$— |
| 1.05 | 3,3,3-trifluoro-propyl- | bond |
| 1.06 | 1-hydroxy-cyclohexyl- | —CH$_2$— |
| 1.07 | 4-methylsulfonyl-phenyl- | —CH$_2$— |
| 1.08 | [1,3]dioxolan-2-yl- | —CH$_2$—CH$_2$— |
| 1.09 | tetrahydro-furan-2-yl- | —CH$_2$— |
| 1.10 | morpholin-4-yl- | —CH$_2$—CH$_2$— |
| 1.11 | phenoxy- | —CH$_2$—CH$_2$— |
| 1.12 | 3-chloro-phenyl- | —CH$_2$— |
| 1.13 | 2,3-dihydro-benzo[1,4]dioxin-6-yl- | —CH$_2$— |
| 1.14 | 4-(1H-pyrazolyl)-phenyl- | —CH$_2$— |

TABLE 1-continued

Table 1 provides 30 compounds of formula (Ia) wherein $G^1$ and $G^2$ are both oxygen, $R^1$ and $R^2$ are both hydrogen, $Q^2$ is 2-ethyl-6-methyl-4-(heptafluoro-prop-2-yl)-phenyl, and $Q^1$, and L have the values listed in the table below.

(Ia)

| Comp No. | $Q^1$ | L |
|---|---|---|
| 1.15 | 1H-indol-3-yl- | —CH$_2$—CH$_2$— |
| 1.16 | 2-(piperidinyl)-phenyl- | —CH$_2$— |
| 1.17 | 2-chloro-pyrid-5-yl- | —CH$_2$— |
| 1.18 | 2-methyl-phenyl- | bond |
| 1.19 | quinolin-5-yl- | bond |
| 1.21 | 4-methyl-thiazol-2-yl- | bond |
| 1.22 | 9H-purin-6-yl- | bond |
| 1.23 | phenyl- | —CH$_2$—CH$_2$— |
| 1.24 | thiophen-2-yl- | —CH$_2$—CH$_2$— |
| 1.25 | 4-methoxy-phenyl- | —CH$_2$— |
| 1.26 | 3-nitro-phenyl- | —CH$_2$— |
| 1.27 | 4-(N,N-dimethylamino)-phenyl- | —CH$_2$— |
| 1.28 | 3,4-dimethoxy-phenyl- | —CH$_2$— |
| 1.29 | benzo[1,3]dioxolan-5-yl- | —CH$_2$— |
| 1.30 | naphth-1-yl- | —CH$_2$— |

Table 2:
Table 2 provides 30 compounds, of formula (Ia) wherein $G^1$ and $G^2$ are both oxygen, $R^1$ and $R^2$ are both hydrogen, $Q^2$ is 2-bromo-6-methyl-4-(heptafluoro-prop-2-yl)-phenyl, and $Q^1$, and L have the values listed in Table 1.

Table 3:
Table 3 provides 30 compounds of formula (Ia) wherein $G^1$ and $G^2$ are both oxygen, $R^1$ and $R^2$ are both hydrogen, $Q^2$ is 2-bromo-6-ethyl-4-(heptafluoro-prop-2-yl)-phenyl, and $Q^1$, and L have the values listed in Table 1.

Table 4:
Table 4 provides 30 compounds of formula (Ia) wherein $G^1$ and $G^2$ are both oxygen, $R^1$ and $R^2$ are both hydrogen, $Q^2$ is 2,6-dichloro-4-(heptafluoro-prop-2-yl)-phenyl, and $Q^1$, and L have the values listed in Table 1.

Table 5:
Table 5 provides 30 compounds of formula (Ia) wherein $G^1$ and $G^2$ are both oxygen, $R^1$ and $R^2$ are both hydrogen, $Q^2$ is 2,6-dibromo-4-(heptafluoro-prop-2-yl)-phenyl, and $Q^1$, and L have the values listed in Table 1.

Table 6:
Table 6 provides 30 compounds of formula (Ia) wherein $G^1$ and $G^2$ are both oxygen, $R^1$ and $R^2$ are both hydrogen, $Q^2$ is 2-bromo-6-chloro-4-(heptafluoro-prop-2-yl)-phenyl, and $Q^1$, and L have the values listed in Table 1.

Table 7:
Table 7 provides 30 compounds of formula (Ia) wherein $G^1$ and $G^2$ are both oxygen, $R^1$ and $R^2$ are both hydrogen, $Q^2$ is 2-ethyl-6-methyl-4-(nonafluoro-but-2-yl)-phenyl, and $Q^1$, and L have the values listed in Table 1.

Table 8:
Table 8 provides 30 compounds of formula (Ia) wherein $G^1$ and $G^2$ are both oxygen, $R^1$ and $R^2$ are both hydrogen, $Q^2$ is 2-bromo-6-methyl-4-(nonafluoro-but-2-yl)-phenyl, and $Q^1$, and L have the values listed in Table 1.

Table 9:
Table 9 provides 30 compounds of formula (Ia) wherein $G^1$ and $G^2$ are both oxygen, $R^1$ and $R^2$ are both hydrogen, $Q^2$ is 2-bromo-6-ethyl-4-(nonafluoro-but-2-yl)-phenyl, and $Q^1$, and L have the values listed in Table 1.

Table 10:
Table 10 provides 30 compounds of formula (Ia) wherein $G^1$ and $G^2$ are both oxygen, $R^1$ and $R^2$ are both hydrogen, $Q^2$ is 2,6-dichloro-4-(nonafluoro-but-2-yl)-phenyl, and $Q^1$, and L have the values listed in Table 1.

Table 11:
Table 11 provides 30 compounds of formula (Ia) wherein $G^1$ and $G^2$ are both oxygen, $R^1$ and $R^2$ are both hydrogen, $Q^2$ is 2,6-dibromo-4-(nonafluoro-but-2-yl)-phenyl, and $Q^1$, and L have the values listed in Table 1.

Table 12:
Table 12 provides 30 compounds of formula (Ia) wherein $G^1$ and $G^2$ are both oxygen, $R^1$ and $R^2$ are both hydrogen, $Q^2$ is $Q^2$ is 2-bromo-6-chloro-4-(nonafluoro-but-2-yl)-phenyl, and $Q^1$, and L have the values listed in Table 1.

The compounds of the invention may be made by a variety of methods, for example as shown in Schemes 1 and 2.

of formula (II) as shown in Scheme 1. When R is OH such reactions are usually carried out in the presence of a coupling reagent, such as DCC(N,N'-dicyclohexylcarbodiimide), EDC (1-ethyl-3-[3-dimethylamino-propyl]carbodiimide hydrochloride) or BOP-Cl (bis(2-oxo-3-oxazolidinyl)phosphonic chloride), in the presence of a base, and optionally in the presence of a nucleophilic catalyst, such as hydroxybenzotriazole. When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_8$alkoxy it is sometimes possible to convert the ester directly to the amide by heating the ester and amine together in a thermal process. Suitable bases include pyridine, triethylamine, 4-(dimethylamino)-pyridine or diisopropylethylamine ("Hunig's base"). Preferred solvents are tetrahydrofuran, dioxane, N,N-dimethylacetamide, 1,2-dimethoxyethane ("glyme"), ethyl acetate or toluene. When R is OH, the reaction is carried out at temperatures of from 0°

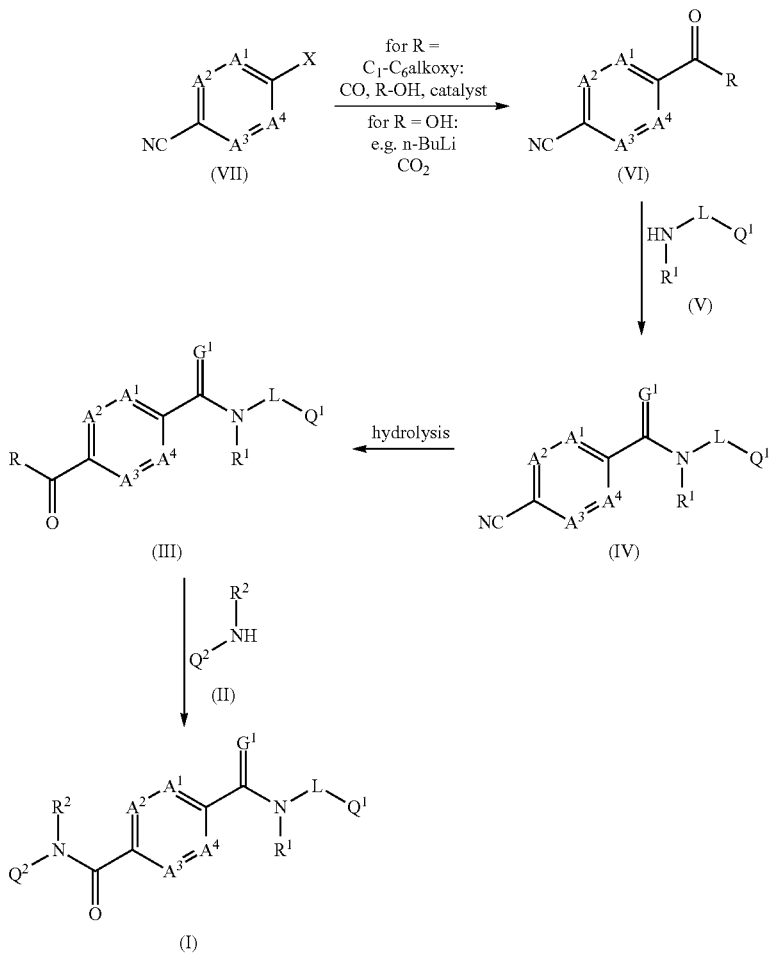

1) Compounds of formula (I), wherein $G^1$ and $G^2$ are oxygen, can be prepared by reacting a compound of formula (III) wherein R is OH, $C_1$-$C_8$alkoxy, or Cl, F or Br, with an amine C. to 150° C., preferably from 50° C. to 120° C., most preferably from 80° C. to 100° C. When R is Cl, the reaction is carried out at temperatures of from 0° C. to 100° C., preferably from 20° C. to 60° C. Amines of formula (II) are known from the literature or can be prepared using known methods.

2) Acid halides of formula (III), wherein R is Cl, F or Br, may be made from carboxylic acids of formula (III), wherein $G^1$ is oxygen and R is OH, under standard conditions, such as treatment with thionyl chloride or oxalyl chloride. A preferred solvent is dichloromethane.

3) Carboxylic acids of formula (III), wherein R is OH, can be prepared by hydrolysis of a cyano compound of formula (IV), under standard conditions, such as such as treatment of the cyano compound with an alkali hydroxide, such as sodium hydroxide, or an acid, such as concentrated sulfuric acid, in a solvent, such as ethanol and/or water. The reaction is carried out at temperatures of from 30° C. to 150° C., preferably from 70° C. to 100° C., most preferably from 80° C. to 90° C.

4) Compounds of formula (IV), wherein $G^1$ is oxygen, can be prepared by reacting an acid derivative of formula (VI) wherein R is OH, $C_1$-$C_8$alkoxy, or Cl, F or Br, with an amine of formula (V) using one of the coupling methods as described in 1). Amines of formula (V) are known from the literature or can be prepared using known methods. A carboxylic acid of formula (VI) wherein R is OH, can be converted into an acid halide of formula (VI) wherein R is Cl, F or Br, for example, using the method as described in 2). A carboxylic ester of formula (VI), wherein R is $C_1$-$C_8$alkoxy, can be converted into a carboxylic acid of formula (VI) wherein R is OH, using standard conditions, such as treatment of the ester with an alkali hydroxide, such as sodium hydroxide, in a solvent, such as ethanol and/or water.

5) Carboxylic esters of formula (VI) wherein R is $C_1$-$C_8$alkoxy, are commercially available or can be prepared by reacting a compound of formula (VII) wherein X is a leaving group, for example a halogen, such as bromo, with carbon monoxide and an alcohol of formula R—OH, such as ethanol, in the presence of a catalyst, such as bis(triphenylphosphine)palladium dichloride, and optionally a base. Suitable bases include pyridine, triethylamine, 4-(dimethylamino)-pyridine or diisopropylethylamine. The reaction is carried out at temperatures of from 50° C. to 200° C., preferably from 100° C. to 150° C., in particular at 115° C. The reaction is carried out at a pressure of from 50 to 200 bar, preferably from 100 to 150 bar, in particular at 120 bar.

6) Alternatively, carboxylic acids of formula (VI) wherein R is OH, are commercially available or can be prepared by reacting a compound of formula (VII) wherein X is a leaving group, for example a halogen, such as bromo, with a organometallic reagent, such as n-butyl lithium, in a halogen-metal exchange reaction and then reacting the intermediate with carbon dioxide. A preferred solvent is tetrahydrofuran. The reaction is carried out at temperatures of from −150° C. to +50° C., preferably from −100° C. to +30° C., in particular at −78° C.

7) Compounds of formula (I), wherein $G^1$ and $G^2$ are sulfur, can be made from a compound of formula (I), wherein $G^1$ and $G^2$ are oxygen, by treatment with a thio-transfer reagent, such as Lawesson's reagent or phosphorus pentasulfide. Compounds of formula (I), wherein $G^1$ is sulfur and $G^2$ is oxygen, can be made by treating a compound of formula (IV), wherein $G^1$ is oxygen, with a thio-transfer reagent, such as Lawesson's reagent or phosphorus pentasulfide prior to the hydrolysis and subsequent coupling with an amine of formula (II).

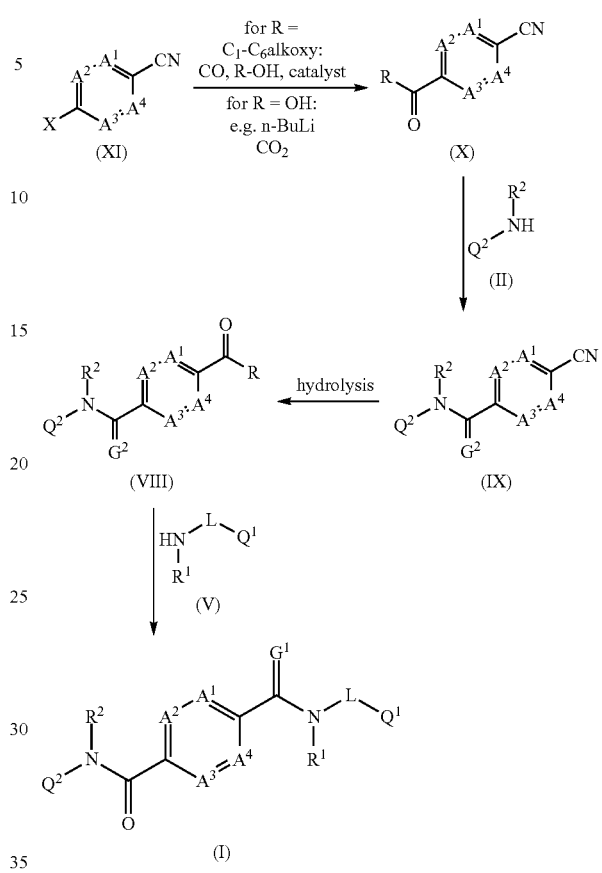

8) Alternatively, compounds of formula (I), wherein $G^1$ and $G^2$ are oxygen, can be prepared by reacting an acid derivative of formula (VIII) wherein R is OH, $C_1$-$C_8$alkoxy, or Cl, F or Br, with an amine of formula (V) as shown in Scheme 2, using one of the coupling methods as described in 1). The different types of acid derivatives of formula (VIII) can be converted into each other, for example, using one of the methods as described in 4).

9) Carboxylic acids of formula (VIII), wherein R is OH, can be prepared by hydrolysis of a cyano compound of formula (IX), as described in 3).

10) Compounds of formula (IX), wherein $G^2$ is oxygen, can be prepared by reacting an acid derivative of formula (X) wherein R is OH, $C_1$-$C_8$alkoxy, or Cl, F or Br, with an amine of formula (II) using one of the coupling methods as described in 1). The different types of acid derivatives of formula (X) can be converted into each other, for example, using one of the methods as described in 4).

11) Carboxylic esters of formula (X) wherein R is $C_1$-$C_8$alkoxy, can be prepared by reacting a compound of formula (XI) wherein X is a leaving group, for example a halogen, such as bromo, using the carbonylation method as described in 5), and carboxylic acids of formula (X) wherein R is OH, can be prepared by reacting a compound of formula (XI) wherein X is a leaving group, for example a halogen, such as bromo, using the carboxylation method as described in 6).

12) Compounds of formula (I), wherein $G^1$ is oxygen and $G^2$ is sulfur, can be made by treating a compound of formula (IX), wherein $G^2$ is oxygen, with a thio-transfer reagent, such as Lawesson's reagent or phosphorus pentasulfide prior to the hydrolysis and subsequent coupling with an amine of formula (V).

The compounds of formula (I) can be used to combat and control infestations of to insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus,* and *R. santonensis*) and the *Termitidae* (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium hydrogen carbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at ambient temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures suitably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)- 2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds such as imidacloprid, thiacloprid, acetamiprid, nitenpyram, dinotefuran or thiamethoxam;

m) Diacylhydrazines, such as tebufenozide, chromafenozide or methoxyfenozide;

n) Diphenyl ethers, such as diofenolan or pyriproxifen;
o) Indoxacarb;
p) Chlorfenapyr;
q) Pymetrozine;
r) Spirotetramat, Spirodiclofen or Spiromesifen; or
s) Flubendiamid or Rynaxypyr In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)—N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrroinitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

Example I1

Preparation of 4-cyano-2-methyl-benzoic acid

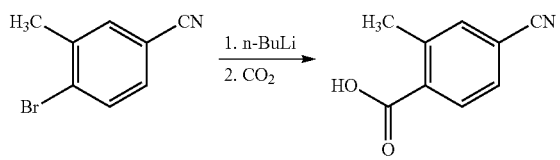

To a solution of 4-bromo-3-methyl-benzonitrile (10.008 g, 51.05 mmol) (commercially available) in tetrahydrofuran ("THF") (350 ml) was added n-butyl lithium (1.6M in THF) (35 ml, 56.16 mmol) at −78° C. The reaction mixture was stirred at −78° C. for 1 hour. Then carbon dioxide (24.933 g, 566.66 mmol) was added. The reaction mixture was allowed to warm to ambient temperature. The reaction mixture was quenched by addition of water (300 ml), and extracted with diethyl ether (3×300 ml). The phases were separated. The aqueous phase was acidified by addition of aqueous hydrochloric acid (concentrated) and extracted with chloroform (3×200 ml). The combined organic phases were concentrated and used without further purification.

Example I2

Preparation of N-butyl-4-cyano-2-methyl-benzamide

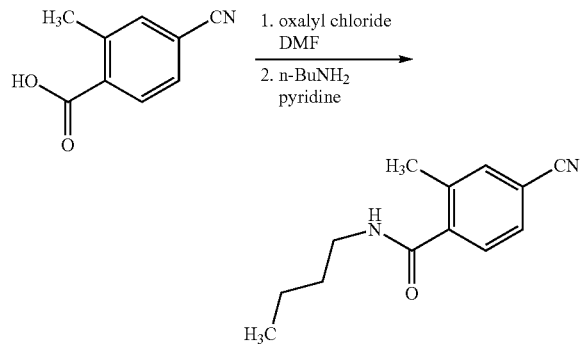

To a solution of 4-cyano-2-methyl-benzoic acid (1.209 g, 7.5 mmol) (Example I1) and N,N-dimethylformamide ("DMF") (2 drops) in dichloromethane (40 ml) under an atmosphere of nitrogen was added oxalyl chloride (0.95 ml, 11.25 mmol). The reaction mixture was stirred for one hour at ambient temperature and then at 60° C. for 1.5 hours. The reaction mixture was concentrated and the residue dissolved in tetrahydrofuran (50 ml). The solution was added drop-wise to a solution of n-butylamine (1.48 mg, 15 mmol) and pyridine (1.81 ml, 22.50 mmol) in tetrahydrofuran (50 ml). The reaction mixture was stirred at ambient temperature for 4 hours. Then the reaction mixture was poured into aqueous sodium hydrogen carbonate (1M) and the mixture extracted three times with ethyl acetate. The combined organic phases were dried over sodium sulfate and concentrated. The residue was purified by column chromatography (eluent: ethyl acetate/cyclohexane 1:2) to give N-butyl-4-cyano-2-methyl-benzamide (0.92 g, 57% yield). $^1$H-NMR (400 MHz, CDCl$_3$): 0.97 (3H, t), 1.42 (2H, m), 1.62 (2H, m), 2.48 (3H, s), 3.45 (2H, q), 5.73 (1H, s), 7.41 (1H, d), 7.48-7.51 (2H, m) ppm.

An analogous procedure was used to prepare the following compound: N-Benzyl-4-cyano-2-methyl-benzamide. $^1$H-NMR (DMSO-d6, 400 MHz): 2.48 (3H, s), 4.62 (2H; s), 6.09 (1H, s), 7.3-7.39 (5H, m), 7.5-7.42 (3H, m) ppm Example I3

Preparation of N-butyl-3-methyl-terephthalamic acid

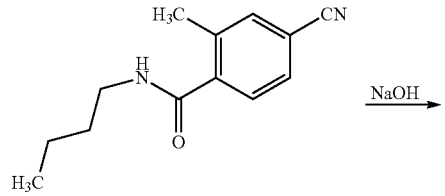

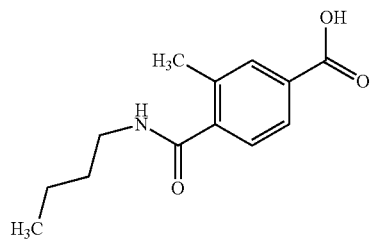

Sodium hydroxide (4.080 g, 102 mmol) was added at ambient temperature to a solution of N-butyl-4-cyano-2-methyl-benzamide (0.919 g, 4.25 mmol) (Example I2) in ethanol (10 ml). The reaction mixture was heated to reflux for 3 hours. The reaction mixture was cooled to ambient temperature and concentrated. The residue was diluted with water and acidified by addition of aqueous hydrochloric acid (concentrated). The precipitate was isolated by filtration and dried at 80° C. for 16 hours to give N-butyl-3-methyl-terephthalamic acid, which was used without further purification. $^1$H-NMR (DMSO-d6, 400 MHz): 0.97 (3H, t), 1.42 (2H, m), 1.62 (2H, m), 2.48 (3H, s), 3.47 (2H, q), 5.73 (1H, s), 7.45 (1H, d), 7.92 (2H, d), 7.5 (1H, s) ppm.

An analogous procedure was used to prepare the following compound: N-Benzyl-3-methyl-terephthalamic acid. $^1$H-NMR (DMSO-d6, 400 MHz): 2.48 (3H, s), 4.62 (2H, d), 6.09 (1H, t), 7.28-7.38 (4H, m), 7.43 (1H, d), 7.88 (1H, d), 7.92 (1H, s) ppm.

Example I4

Preparation of 4-cyano-N-[2-ethyl-4-(1,2,2,3,3,3-hexafluoro-1-trifluoromethyl-propyl)-6-methyl-phenyl]-3-methyl-benzamide

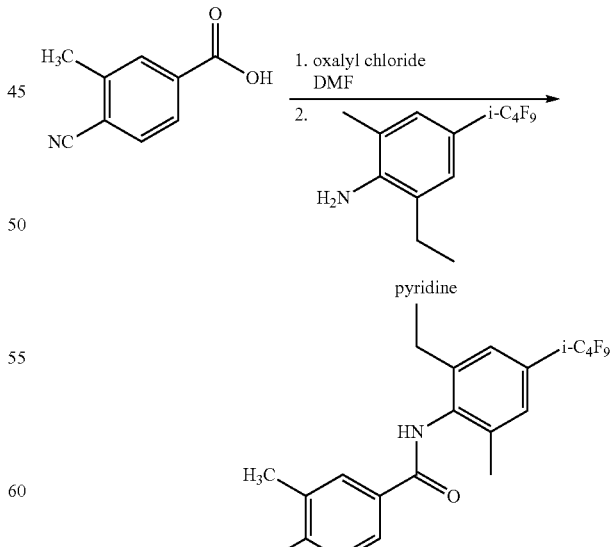

To a solution of 4-cyano-3-methyl-benzoic acid (6.64 g, 41.20 mmol) (prepared according to Bioorganic & Medicinal Chemistry Letters 2004, 14(17), 4585-4589 or EP 1,512,687)

and N,N-dimethylformamide ("DMF") (few drops) in dichloromethane (200 ml) under an atmosphere of nitrogen was added oxalyl chloride (4.18 ml, 49.44 mmol). The reaction mixture was stirred for one hour at ambient temperature and then for 1.5 hours at 60° C. The reaction mixture was concentrated and the residue dissolved in tetrahydrofuran (200 ml). The solution was added drop-wise to a solution of 2-methyl-6-ethyl-4-(heptafluoro-prop-2-yl)-aniline (prepared according to EP 1,006,102) (10.910 g, 30.90 mmol) and pyridine (3.31 ml, 41.20 mmol) in tetrahydrofuran (200 ml). The reaction mixture was stirred for 16 hours at 90° C. Then the reaction mixture was poured into aqueous sodium hydrogen carbonate (1M) and the mixture extracted three times with ethyl acetate. The combined organic phases were dried over sodium sulfate and concentrated. The residue was purified by column chromatography (eluent: ethyl acetate/cyclohexane 1:3) to give the desired compound (15.34 g, 94% yield). $^1$H-NMR (400 MHz, CDCl$_3$): 7.90 (1H, s), 7.78 (2H, m), 7.53 (1H, s), 7.39 (2H, s), 2.67 (5H, s), 2.35 (3H, s), 1.16 (3H, t) ppm.

Example I5

Preparation of N-[2-ethyl-4-(1,2,2,3,3,3-hexafluoro-1-trifluoromethyl-propyl)-6-methyl-phenyl]-2-methyl-terephthalamic acid

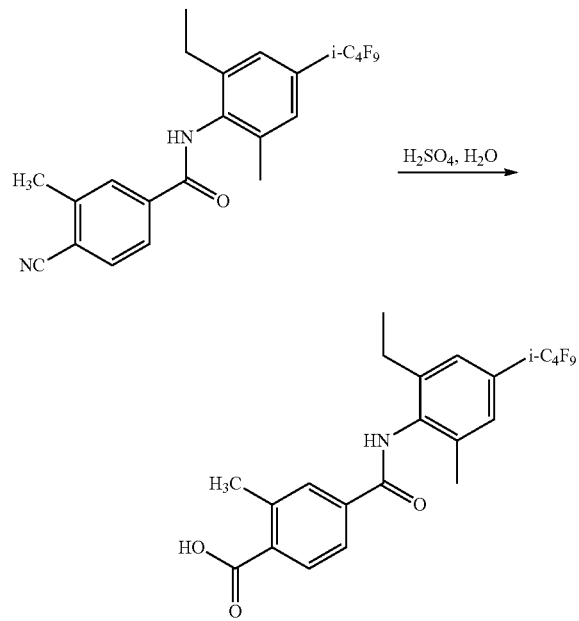

To a solution of 4-cyano-N-[2-ethyl-4-(1,2,2,3,3,3-hexafluoro-1-trifluoromethyl-propyl)-6-methyl-phenyl]-3-methyl-benzamide (Example I4) (5 g, 10 mmol) in water (3 ml) was added concentrated sulfuric acid (26.84 ml). The reaction mixture was stirred for 28 days at 90° C., wherein more concentrated sulfuric acid (26.84 ml) was added once a week. The solution was extracted with diethyl ether and the acid was used without any further purification.

Example P1

Preparation of N-1-butyl-N-4-[2,6-dimethyl-4-(1,2,2,2-tetrafluoro-1-trifluoro-methyl-ethyl)-phenyl]-2-methyl-terephthalamide (Compound No. A1 of Table A)

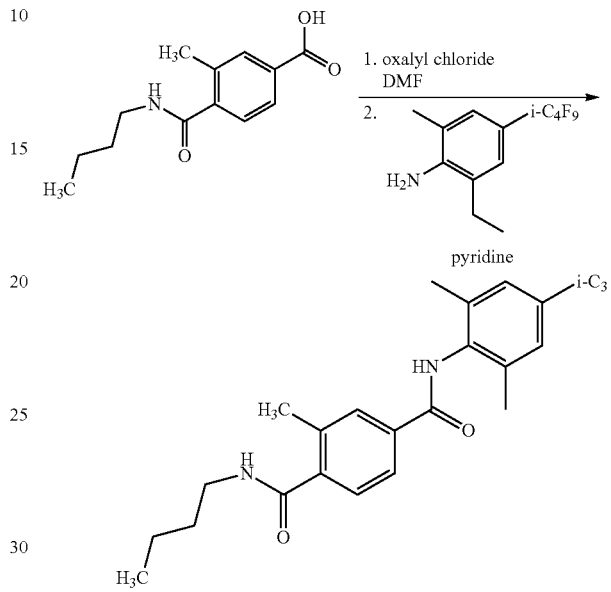

To a solution of N-butyl-3-methyl-terephthalamic acid (0.452 g, 1.92 mmol) (Example 13) and N,N-dimethylformamide ("DMF") (2 drops) in dichloromethane (10 ml) under an atmosphere of nitrogen was added oxalyl chloride (0.24 ml, 2.88 mmol). The reaction mixture was stirred for one hour at ambient temperature and then at 60° C. for 1.5 hours. The reaction mixture was concentrated and the residue dissolved in tetrahydrofuran (25 ml). The solution was added drop-wise to a solution of 2,6-dimethyl-4-(heptafluoro-prop-2-yl)-aniline (prepared according to EP 1,006,102) (0.499 g, 1.73 mmol) and pyridine (0.46 ml, 5.76 mmol) in tetrahydrofuran (25 ml). The reaction mixture was stirred at ambient temperature for 16 hours. Then the reaction mixture was poured into aqueous sodium hydrogen carbonate (1M) and the mixture extracted three times with ethyl acetate. The combined organic phases were dried over sodium sulfate and concentrated. The residue was purified by column chromatography (eluent: ethyl acetate/cyclohexane 1:1) to give Compound No. A1 of Table A (0.055 g, 6% yield). 1H-NMR (400 MHz, CHCl3) 0.98 (3H, t), 1.41 (2H, m), 1.59 (2H, m), 2.44 (6H, s), 2.48 (3H, s), 3.42 (2H, q), 5.70 (1H, s), 7.81 (2H, s), 7.38 (2H, m), 7.47 (1H, s), 7.50 (1H, d).

Analogous procedures were used to prepare the following compounds:

N-1-Benzyl-N-4-[2,6-dimethyl-4-(1,2,2,2-tetrafluoro-1-trifluoromethyl-ethyl)-phenyl]-2-methyl-terephthalamide. Compound No. A2 of Table A. 1H-NMR (400 MHz, CHCl3) 2.31 (6H, s), 2.5 (3H, s), 4.62 (2H, d), 6.19 (1H, t), 7.35 (6H, m), 7.45 (1H, d), 7.52 (1H, s), 7.70 (1H, d), 7.75 (1H, s).

N-1-Butyl-N-4-[2-ethyl-4-(1,2,2,3,3,3-hexafluoro-1-trifluoromethyl-propyl)-6-methyl-phenyl]-2-methyl-terephthalamide. Compound No. A3 of Table A. 1H-NMR (400 MHz, CHCl3) 0.98 (3H, t), 1.21 (3H, t), 1.43 (2H, m), 1.62

(2H, m), 2.34 (3H, s), 2.52 (3H, s), 2.68 (2H, q), 3.45 (2H, q), 5.73 (1H, s), 7.36 (3H, m), 7.46 (1H, d), 7.74 (2H, d), 7.78 (1H, s).

N-1-Benzyl-N-4-[2-ethyl-4-(1,2,2,3,3,3-hexafluoro-1-trifluoromethyl-propyl)-6-methyl-phenyl]-2-methyl-terephthalamide. Compound No. A4 of Table A. 1H-NMR (400 MHz, CHCl3) 1.19 (3H, t), 2.34 (3H, s), 2.52 (3H, s), 2.70 (2H, q), 4.65 (2H, d), 5.12 (1H, t), 7.28-7.50 (8H, m), 7.72 (1H, d), 7.79 (1H, s).

Example P2

Preparation of N-1-L-Q1-N'-4-[2-ethyl-4-(1,2,2,3,3,3-hexafluoro-1-trifluoro-methyl-propyl)-6-methyl-phenyl]-2-methyl-terephthalamide

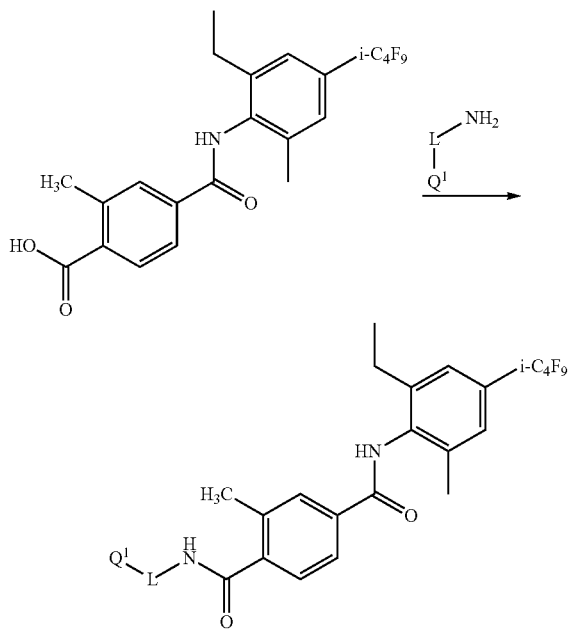

Method A and method B were used to prepare a number of compounds (Compound No. A4 to A104 of Table A) in parallel.

Method A: A solution of an amine (0.03 mmol in 120 μl of N,N-dimethylacetamide) was added to each well of a 96-well plate, followed by Hunig's base (40 μl), a solution of the acid (0.045 mmol of N-[2-ethyl-4-(1,2,2,3,3,3-hexafluoro-1-trifluoromethyl-propyl)-6-methyl-phenyl]-2-methyl-terephthalamic acid, made according to Example I5, in 0.4 ml of N,N-dimethylacetamide), and a solution of bis(2-oxo-3-oxazolidinyl)phosphonic chloride ("BOP-Cl") (0.06 ml in 0.2 ml of N,N-dimethylacetamide). The reaction mixtures were stirred for 16 hours at 80° C., then the solvent was evaporated. The mixtures were diluted with acetonitrile and purified by HPLC to give the compounds of Table A.

Method B: A solution of an amine (0.03 mmol in 400 μl of N,N-dimethylacetamide) was added to each test tube, followed by Hunig's base (40 μl), a solution of the acid (0.045 mmol of N-[2-ethyl-4-(1,2,2,3,3,3-hexafluoro-1-trifluoromethyl-propyl)-6-methyl-phenyl]-2-methyl-terephthalamic acid, made according to Example I5, in 0.4 ml of N,N-dimethyl-acetamide), and a solution of bis(2-oxo-3-oxazolidinyl) phosphonic chloride ("BOP-Cl") (0.06 mmol in 0.2 ml of N,N-dimethylacetamide). The reaction mixtures were stirred for 16 hours at 100° C., then the solvent was evaporated. The mixtures were diluted with acetonitrile and purified by HPLC to give the compounds of Table A.

The following method was used for HPLC-MS analysis for Compound No. A4 to A104 of Table A:

Method (Waters Alliance 2795 LC) with the following HPLC gradient conditions (Solvent A: 0.1% of formic acid in water/acetonitrile (9:1) and Solvent B: 0.1% of formic acid in acetonitrile)

| Time (minutes) | A (%) | B (%) | Flow rate (ml/min) |
|---|---|---|---|
| 0 | 90 | 10 | 1.7 |
| 2.5 | 0 | 100 | 1.7 |
| 2.8 | 0 | 100 | 1.7 |
| 2.9 | 90 | 10 | 1.7 |

Type of column: Water atlantis dc18; Column length: 20 mm; Internal diameter of column: 3 mm; Particle Size: 3 micron; Temperature: 40° C. "RT" means retention time.

TABLE A

Table A provides 107 compounds of formula (Ia) wherein $G^1$ and $G^2$ are both oxygen, $R^1$ and $R^2$ are both hydrogen, and $Q^1$, L and $Q^2$ have the values listed in the table below.

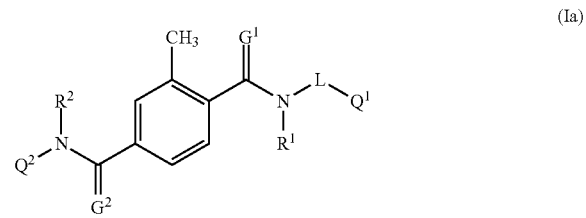

(Ia)

| Comp No. | $Q^1$ | L | $Q^2$ | MH+ | RT (minutes) |
|---|---|---|---|---|---|
| A1 | n-butyl- | bond | 2,6-dimethyl-4-(heptafluoro-prop-2-yl)-phenyl- | — | — |
| A2 | phenyl- | —CH₂— | 2,6-dimethyl-4-(heptafluoro-prop-2-yl)-phenyl- | — | — |

TABLE A-continued

Table A provides 107 compounds of formula (Ia) wherein $G^1$ and $G^2$ are both oxygen, $R^1$ and $R^2$ are both hydrogen, and $Q^1$, L and $Q^2$ have the values listed in the table below.

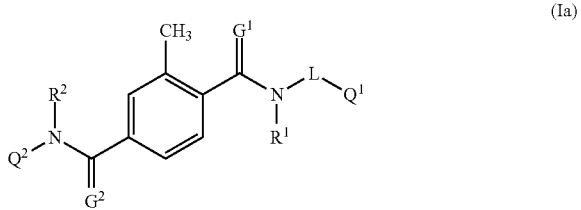

(Ia)

| Comp No. | $Q^1$ | L | $Q^2$ | MH+ | RT (minutes) |
|---|---|---|---|---|---|
| A3 | n-butyl- | bond | 2-ethyl-6-methyl-4-(nonafluoro-but-2-yl)-phenyl- | — | — |
| A4 | phenyl- | —CH$_2$— | 2-ethyl-6-methyl-4-(nonafluoro-but-2-yl)-phenyl- | 605.18 | 2.01 |
| A5 | 4-chloro-phenyl- | —CH$_2$— | 2-ethyl-6-methyl-4-(nonafluoro-but-2-yl)-phenyl- | 639.14 | 2.12 |
| A6 | pyrid-2-yl- | —CH$_2$— | 2-ethyl-6-methyl-4-(nonafluoro-but-2-yl)-phenyl- | 606.17 | 1.53 |
| A7 | pyrid-3-yl- | —CH$_2$— | 2-ethyl-6-methyl-4-(nonafluoro-but-2-yl)-phenyl- | 606.17 | 1.35 |
| A8 | 1-methyl-1H-imidazol-4-yl- | —CH$_2$— | 2-ethyl-6-methyl-4-(nonafluoro-but-2-yl)-phenyl- | 609.18 | 1.22 |
| A9 | 1H-benzimidazol-2-yl- | —CH$_2$— | 2-ethyl-6-methyl-4-(nonafluoro-but-2-yl)-phenyl- | 645.18 | 1.8 |
| A10 | 3,3,3-trifluoro-propyl- | bond | 2-ethyl-6-methyl-4-(nonafluoro-but-2-yl)-phenyl- | 611.15 | 1.95 |
| A11 | 1-hydroxy-cyclohexyl- | —CH$_2$— | 2-ethyl-6-methyl-4-(nonafluoro-but-2-yl)-phenyl- | 627.22 | 1.88 |
| A12 | 6-ethoxycarbonyl-cyclohex-3-en-1-yl- | bond | 2-ethyl-6-methyl-4-(nonafluoro-but-2-yl)-phenyl- | 667.21 | 2.07 |
| A13 | benzo[1,3]-dioxolan-5-yl- | —CH$_2$—CH$_2$— | 2-ethyl-6-methyl-4-(nonafluoro-but-2-yl)-phenyl- | 663.18 | 2.07 |
| A14 | 3-chloro-5-trifluoromethyl-pyrid-2-yl- | —CH$_2$— | 2-ethyl-6-methyl-4-(nonafluoro-but-2-yl)-phenyl- | 708.12 | 2.15 |
| A15 | 4-methylsulfonyl-phenyl- | —CH$_2$— | 2-ethyl-6-methyl-4-(nonafluoro-but-2-yl)-phenyl- | 683.15 | 1.79 |
| A16 | 1-hydroxy-but-2-yl- | bond | 2-ethyl-6-methyl-4-(nonafluoro-but-2-yl)-phenyl- | 587.19 | 1.71 |
| A17 | 1-methoxy-prop-2-yl- | bond | 2-ethyl-6-methyl-4-(nonafluoro-but-2-yl)-phenyl- | 587.19 | 1.83 |
| A18 | 2-bromo-phenyl- | —CH$_2$— | 2-ethyl-6-methyl-4-(nonafluoro-but-2-yl)-phenyl- | 683.09 | 2.12 |
| A19 | [1,3]dioxolan-2-yl- | —CH$_2$—CH$_2$— | 2-ethyl-6-methyl-4-(nonafluoro-but-2-yl)-phenyl- | 615.18 | 1.8 |
| A20 | tetrahydro-furan-2-yl- | —CH$_2$— | 2-ethyl-6-methyl-4-(nonafluoro-but-2-yl)-phenyl- | 599.19 | 1.83 |
| A21 | 2-methyl-cyclohex-1-yl- | bond | 2-ethyl-6-methyl-4-(nonafluoro-but-2-yl)-phenyl- | 611.22 | 2.15 |
| A22 | morpholin-4-yl- | —CH$_2$—CH$_2$— | 2-ethyl-6-methyl-4-(nonafluoro-but-2-yl)-phenyl- | 628.21 | 1.24 |
| A23 | pyrrolidinyl- | —(CH$_2$)$_3$— | 2-ethyl-6-methyl-4-(nonafluoro-but-2-yl)-phenyl- | 626.24 | 1.25 |

TABLE A-continued

Table A provides 107 compounds of formula (Ia) wherein $G^1$ and $G^2$ are both oxygen, $R^1$ and $R^2$ are both hydrogen, and $Q^1$, L and $Q^2$ have the values listed in the table below.

(Ia)

| Comp No. | $Q^1$ | L | $Q^2$ | MH$^+$ | RT (minutes) |
|---|---|---|---|---|---|
| A24 | 2-(HOSO$_2$—S)-eth-1-yl- | bond | 2-ethyl-6-methyl-4-(nonafluoro-but-2-yl)-phenyl- | 655.09 | 1.47 |
| A25 | phenoxy- | —CH$_2$—CH$_2$— | 2-ethyl-6-methyl-4-(nonafluoro-but-2-yl)-phenyl- | 635.19 | 2.04 |
| A26 | 3-chloro-phenyl- | —CH$_2$— | 2-ethyl-6-methyl-4-(nonafluoro-but-2-yl)-phenyl- | 639.14 | 2.12 |
| A27 | 2,3-dihydro-benzo[1,4]dioxin-6-yl- | —CH$_2$— | 2-ethyl-6-methyl-4-(nonafluoro-but-2-yl)-phenyl- | 663.18 | 2.0 |
| A28 | 2-(N-(methyl-carbonyl)amino)-eth-1-yl- | bond | 2-ethyl-6-methyl-4-(nonafluoro-but-2-yl)-phenyl- | 600.18 | 1.57 |
| A29 | 4-(1H-pyrazolyl)-phenyl- | —CH$_2$— | 2-ethyl-6-methyl-4-(nonafluoro-but-2-yl)-phenyl- | 671.2 | 1.99 |
| A30 | 2-trifluoro-methoxy-phenyl- | —CH$_2$— | 2-ethyl-6-methyl-4-(nonafluoro-but-2-yl)-phenyl- | 689.16 | 2.19 |
| A31 | 1H-indol-3-yl- | —CH$_2$—CH$_2$— | 2-ethyl-6-methyl-4-(nonafluoro-but-2-yl)-phenyl- | 658.2 | 1.99 |
| A32 | 2-trifluoromethyl-phenyl- | —CH$_2$— | 2-ethyl-6-methyl-4-(nonafluoro-but-2-yl)-phenyl- | 673.16 | 2.15 |
| A33 | 2-(piperidinyl)-phenyl- | —CH$_2$— | 2-ethyl-6-methyl-4-(nonafluoro-but-2-yl)-phenyl- | 688.25 | 1.64 |
| A34 | 4-phenoxy-phenyl- | —CH$_2$— | 2-ethyl-6-methyl-4-(nonafluoro-but-2-yl)-phenyl- | 697.2 | 2.32 |
| A35 | 2-chloro-pyrid-5-yl- | —CH$_2$— | 2-ethyl-6-methyl-4-(nonafluoro-but-2-yl)-phenyl- | 640.13 | 1.88 |
| A36 | 1-(benzyl)-pyrrolidin-3-yl | bond | 2-ethyl-6-methyl-4-(nonafluoro-but-2-yl)-phenyl- | 674.24 | 1.37 |
| A37 | 1-(benzyl)-piperazin-4-yl- | —CH$_2$—CH$_2$— | 2-ethyl-6-methyl-4-(nonafluoro-but-2-yl)-phenyl- | 717.28 | 1.35 |
| A38 | furan-2-yl- | —CH$_2$— | 2-ethyl-6-methyl-4-(nonafluoro-but-2-yl)-phenyl- | 595.16 | 1.93 |
| A39 | 4-(prop-2-yl)-phenyl- | bond | 2-ethyl-6-methyl-4-(nonafluoro-but-2-yl)-phenyl- | 633.21 | 2.31 |
| A40 | 2-methyl-phenyl- | bond | 2-ethyl-6-methyl-4-(nonafluoro-but-2-yl)-phenyl- | 605.18 | 2.07 |
| A41 | quinolin-5-yl- | bond | 2-ethyl-6-methyl-4-(nonafluoro-but-2-yl)-phenyl- | 642.17 | 1.71 |
| A42 | 2,4-dimethoxy-phenyl- | bond | 2-ethyl-6-methyl-4-(nonafluoro-but-2-yl)-phenyl- | 651.18 | 2.09 |
| A43 | 3-fluoro-phenyl- | bond | 2-ethyl-6-methyl-4-(nonafluoro-but-2-yl)-phenyl- | 609.15 | 1.88 |
| A44 | 1H-indazol-5-yl- | bond | 2-ethyl-6-methyl-4-(nonafluoro-but-2-yl)-phenyl- | 631.17 | 1.88 |

TABLE A-continued

Table A provides 107 compounds of formula (Ia) wherein $G^1$ and $G^2$ are both oxygen, $R^1$ and $R^2$ are both hydrogen, and $Q^1$, L and $Q^2$ have the values listed in the table below.

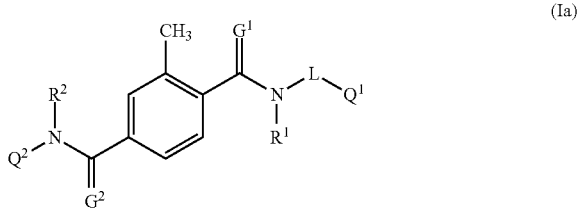

(Ia)

| Comp No. | $Q^1$ | L | $Q^2$ | MH+ | RT (minutes) |
|---|---|---|---|---|---|
| A45 | 4-(pyrrolyl)-phenyl- | bond | 2-ethyl-6-methyl-4-(nonafluoro-but-2-yl)-phenyl- | 656.19 | 2.17 |
| A46 | 4-(piperidinyl)-phenyl- | bond | 2-ethyl-6-methyl-4-(nonafluoro-but-2-yl)-phenyl- | 674.24 | 1.51 |
| A47 | 2-methoxy-5-(phenyl)-phenyl- | bond | 2-ethyl-6-methyl-4-(nonafluoro-but-2-yl)-phenyl- | 697.2 | 2.41 |
| A48 | 2-methylthio-phenyl- | bond | 2-ethyl-6-methyl-4-(nonafluoro-but-2-yl)-phenyl- | 637.15 | 2.16 |
| A49 | benzothiazol-6-yl- | bond | 2-ethyl-6-methyl-4-(nonafluoro-but-2-yl)-phenyl- | 648.13 | 1.99 |
| A50 | 2-(morpholin-4-yl)-5-trifluoro-methyl-phenyl- | bond | 2-ethyl-6-methyl-4-(nonafluoro-but-2-yl)-phenyl- | 744.2 | 2.33 |
| A51 | 2-(1H-indol-2-yl)-phenyl- | bond | 2-ethyl-6-methyl-4-(nonafluoro-but-2-yl)-phenyl- | 706.2 | 2.23 |
| A52 | 2-(morpholin-4-yl)-phenyl- | bond | 2-ethyl-6-methyl-4-(nonafluoro-but-2-yl)-phenyl- | 676.21 | 2.17 |
| A53 | 2,3-dihydro-benzofuran-5-yl- | —CH$_2$— | 2-ethyl-6-methyl-4-(nonafluoro-but-2-yl)-phenyl- | 647.19 | 1.97 |
| A54 | 2,5-dimethyl-2H-pyrazol-3-yl- | bond | 2-ethyl-6-methyl-4-(nonafluoro-but-2-yl)-phenyl- | 609.18 | 1.81 |
| A55 | 4-methyl-thiazol-2-yl- | bond | 2-ethyl-6-methyl-4-(nonafluoro-but-2-yl)-phenyl- | 612.13 | 2.03 |
| A56 | 5-methylthio-1H-[1,2,4]triazol-3-yl- | bond | 2-ethyl-6-methyl-4-(nonafluoro-but-2-yl)-phenyl- | 628.14 | 1.97 |
| A57 | 3-methyl-pyrid-2-yl- | bond | 2-ethyl-6-methyl-4-(nonafluoro-but-2-yl)-phenyl- | 606.17 | 1.75 |
| A58 | quinolin-2-yl- | bond | 2-ethyl-6-methyl-4-(nonafluoro-but-2-yl)-phenyl- | 642.17 | 2.11 |
| A59 | 5-methyl-3-(phenyl)-isoxazol-4-yl- | bond | 2-ethyl-6-methyl-4-(nonafluoro-but-2-yl)-phenyl- | 672.18 | 2.04 |
| A60 | 9H-purin-6-yl- | bond | 2-ethyl-6-methyl-4-(nonafluoro-but-2-yl)-phenyl- | 633.16 | 1.65 |
| A61 | 5-(phenyl)-1H-pyrazol-3-yl- | bond | 2-ethyl-6-methyl-4-(nonafluoro-but-2-yl)-phenyl- | 657.18 | 2.01 |
| A62 | 4-methyl-benzothiazol-2-yl- | bond | 2-ethyl-6-methyl-4-(nonafluoro-but-2-yl)-phenyl- | 662.14 | 2.29 |
| A63 | 5-methyl-[1,3,4]-thiadiazol-2-yl- | bond | 2-ethyl-6-methyl-4-(nonafluoro-but-2-yl)-phenyl- | 613.12 | 1.87 |
| A64 | 2-(phenoxy)-pyrid-5-yl- | bond | 2-ethyl-6-methyl-4-(nonafluoro-but-2-yl)-phenyl- | 684.18 | 2.15 |
| A65 | 4,6-dimethyl-2H-pyrazolo[3,4-b]-pyrid-3-yl- | bond | 2-ethyl-6-methyl-4-(nonafluoro-but-2-yl)-phenyl- | 660.19 | 1.89 |

TABLE A-continued

Table A provides 107 compounds of formula (Ia) wherein $G^1$ and $G^2$ are both oxygen, $R^1$ and $R^2$ are both hydrogen, and $Q^1$, L and $Q^2$ have the values listed in the table below.

(Ia)

| Comp No. | $Q^1$ | L | $Q^2$ | MH$^+$ | RT (minutes) |
|---|---|---|---|---|---|
| A66 | 4-(4-methyl-phenyl)-thiazol-2-yl- | bond | 2-ethyl-6-methyl-4-(nonafluoro-but-2-yl)-phenyl- | 688.16 | 2.28 |
| A67 | piperidinyl- | —(CH$_2$)$_3$— | 2-ethyl-6-methyl-4-(nonafluoro-but-2-yl)-phenyl- | 640.25 | 1.25 |
| A68 | 3-(4-chloro-phenyl)-isoxazol-5-yl- | —CH$_2$— | 2-ethyl-6-methyl-4-(nonafluoro-but-2-yl)-phenyl- | 706.14 | 2.23 |
| A69 | 2-fluoro-phenyl- | —CH$_2$— | 2-ethyl-6-methyl-4-(nonafluoro-but-2-yl)-phenyl- | 623.17 | 2.04 |
| A70 | phenyl- | —CH(CH$_3$)— | 2-ethyl-6-methyl-4-(nonafluoro-but-2-yl)-phenyl- | 619.19 | 2.07 |
| A71 | phenyl- | —CH$_2$—CH$_2$— | 2-ethyl-6-methyl-4-(nonafluoro-but-2-yl)-phenyl- | 619.19 | 2.07 |
| A72 | 1,2,2,6,6-pentamethyl-piperidin-4-yl- | bond | 2-ethyl-6-methyl-4-(nonafluoro-but-2-yl)-phenyl- | 668.28 | 1.28 |
| A73 | thiophen-2-yl- | —CH$_2$—CH$_2$— | 2-ethyl-6-methyl-4-(nonafluoro-but-2-yl)-phenyl- | 625.15 | 2.04 |
| A74 | thiophen-2-yl- | —CH$_2$— | 2-ethyl-6-methyl-4-(nonafluoro-but-2-yl)-phenyl- | 611.13 | 2 |
| A75 | 4-methoxy-phenyl- | —CH$_2$— | 2-ethyl-6-methyl-4-(nonafluoro-but-2-yl)-phenyl- | 635.19 | 2.01 |
| A76 | 4-fluoro-phenyl- | —CH$_2$— | 2-ethyl-6-methyl-4-(nonafluoro-but-2-yl)-phenyl- | 623.17 | 2.01 |
| A77 | 2,4-dimethoxy-phenyl- | —CH$_2$— | 2-ethyl-6-methyl-4-(nonafluoro-but-2-yl)-phenyl- | 665.2 | 2.09 |
| A78 | 2-methoxy-phenyl- | —CH$_2$— | 2-ethyl-6-methyl-4-(nonafluoro-but-2-yl)-phenyl- | 635.19 | 2.03 |
| A79 | 2-trifluoromethyl-pyrid-5-yl- | —CH$_2$— | 2-ethyl-6-methyl-4-(nonafluoro-but-2-yl)-phenyl- | 674.16 | 2.01 |
| A80 | 3-trifluoromethyl-phenyl- | CH$_2$— | 2-ethyl-6-methyl-4-(nonafluoro-but-2-yl)-phenyl- | 673.16 | 2.15 |
| A81 | 4-(2-methyl-prop-2-yl)-phenyl- | —CH$_2$— | 2-ethyl-6-methyl-4-(nonafluoro-but-2-yl)-phenyl- | 661.24 | 2.27 |
| A82 | 3-iodo-phenyl- | —CH$_2$— | 2-ethyl-6-methyl-4-(nonafluoro-but-2-yl)-phenyl- | 731.07 | 2.17 |
| A83 | 4-bromo-2-fluoro-phenyl- | —CH$_2$— | 2-ethyl-6-methyl-4-(nonafluoro-but-2-yl)-phenyl- | 701.08 | 2.15 |
| A84 | 2,4-dichloro-phenyl- | —CH$_2$— | 2-ethyl-6-methyl-4-(nonafluoro-but-2-yl)-phenyl- | 673.1 | 2.25 |
| A85 | 3-methyl-phenyl- | —CH$_2$— | 2-ethyl-6-methyl-4-(nonafluoro-but-2-yl)-phenyl- | 619.19 | 2.08 |

TABLE A-continued

Table A provides 107 compounds of formula (Ia) wherein $G^1$ and $G^2$ are both oxygen, $R^1$ and $R^2$ are both hydrogen, and $Q^1$, L and $Q^2$ have the values listed in the table below.

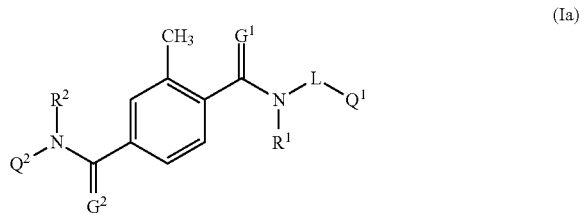

(Ia)

| Comp No. | $Q^1$ | L | $Q^2$ | $MH^+$ | RT (minutes) |
|---|---|---|---|---|---|
| A86 | 2-ethoxy-phenyl- | —CH$_2$— | 2-ethyl-6-methyl-4-(nonafluoro-but-2-yl)-phenyl- | 649.2 | 2.15 |
| A87 | 2-chloro-6-methyl-phenyl- | —CH$_2$— | 2-ethyl-6-methyl-4-(nonafluoro-but-2-yl)-phenyl- | 653.15 | 2.16 |
| A88 | 3-nitro-phenyl- | —CH$_2$— | 2-ethyl-6-methyl-4-(nonafluoro-but-2-yl)-phenyl- | 650.16 | 2.04 |
| A89 | 4-iodo-phenyl- | —CH$_2$— | 2-ethyl-6-methyl-4-(nonafluoro-but-2-yl)-phenyl- | 731.07 | 2.19 |
| A90 | 4-(phenyl)-phenyl- | —CH$_2$— | 2-ethyl-6-methyl-4-(nonafluoro-but-2-yl)-phenyl- | 681.21 | 2.21 |
| A91 | 3,4-dimethyl-phenyl- | —CH$_2$— | 2-ethyl-6-methyl-4-(nonafluoro-but-2-yl)-phenyl- | 633.21 | 2.19 |
| A92 | 4-(N,N-dimethyl-amino)-phenyl- | —CH$_2$— | 2-ethyl-6-methyl-4-(nonafluoro-but-2-yl)-phenyl- | 648.22 | 1.64 |
| A93 | 4-(4-chloro-phenoxy)-phenyl- | —CH$_2$— | 2-ethyl-6-methyl-4-(nonafluoro-but-2-yl)-phenyl- | 731.16 | 2.29 |
| A94 | 3,4-dimethoxy-phenyl- | —CH$_2$— | 2-ethyl-6-methyl-4-(nonafluoro-but-2-yl)-phenyl- | 665.2 | 1.92 |
| A95 | 3,5-bis(trifluoro-methyl)-phenyl- | —CH$_2$— | 2-ethyl-6-methyl-4-(nonafluoro-but-2-yl)-phenyl- | 741.15 | 2.24 |
| A96 | benzo[1,3]dioxo-lan-5-yl- | —CH$_2$— | 2-ethyl-6-methyl-4-(nonafluoro-but-2-yl)-phenyl- | 649.17 | 1.99 |
| A97 | 3-fluoro-phenyl- | —CH$_2$— | 2-ethyl-6-methyl-4-(nonafluoro-but-2-yl)-phenyl- | 623.17 | 2.03 |
| A98 | naphth-1-yl- | —CH$_2$— | 2-ethyl-6-methyl-4-(nonafluoro-but-2-yl)-phenyl- | 655.19 | 2.16 |
| A99 | 2-chloro-phenyl- | —CH$_2$— | 2-ethyl-6-methyl-4-(nonafluoro-but-2-yl)-phenyl- | 639.14 | 2.11 |
| A100 | 3,4-dichloro-phenyl- | —CH$_2$— | 2-ethyl-6-methyl-4-(nonafluoro-but-2-yl)-phenyl- | 673.1 | 2.21 |
| A101 | 4-methyl-phenyl- | —CH$_2$— | 2-ethyl-6-methyl-4-(nonafluoro-but-2-yl)-phenyl- | 619.19 | 2.07 |
| A102 | 2,4-difluoro-phenyl- | —CH$_2$— | 2-ethyl-6-methyl-4-(nonafluoro-but-2-yl)-phenyl- | 641.16 | 2.05 |
| A103 | 3,4,5-trimethoxy-phenyl- | —CH$_2$— | 2-ethyl-6-methyl-4-(nonafluoro-but-2-yl)-phenyl- | 695.21 | 1.96 |
| A104 | pyrid-4-yl- | —CH$_2$— | 2-ethyl-6-methyl-4-(nonafluoro-but-2-yl)-phenyl- | 606.17 | 1.31 |

BIOLOGICAL EXAMPLES

This Example illustrates the pesticidal/insecticidal properties of compounds of formula (I). The tests were performed as follows:

Spodoptera littoralis (Egyptian Cotton Leafworm)
Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT). The following compounds gave at least 80% control of Spodoptera littoralis: A2, A6, A8, A9, A10, A11, A13, A15, A19, A20, A22, A25, A27, A29, A31, A33, A35, A41, A50, A55, A60, A65, A73, A88, A92, and A94.

Heliothis virescens (Tobacco Budworm):
Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality and growth regulation.
The following compounds gave at least 80% control of Heliothis virescens: A2, A3, A4, A5, A6, A7, A9, A10, A11, A13, A15, A19, A20, A22, A25, A26, A27, A28, A29, A31, A32, A33, A35, A38, A40, A41, A43, A46, A55, A59, A60, A65, A69, A70, A71, A73, A74, A75, A77, A79, A80, A82, A86, A88, A89, A90, A92, A94, A96, A98, and A100.

Plutella xylostella (Diamond Back Moth):
A 24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.
The following compounds gave at least 80% control of Plutella xylostella: A3, A4, A5, A6, A7, A8, A10, A15, A16, A18, A19, A20, A22, A25, A26, A27, A28, A29, A31, A32, A33, A35, A38, A40, A55, A69, A71, A73, A74, A75, A76, A77, A78, A80, A82, A86, A87, A88, A89, A92, A94, A96, A97, A98, and A99.

Diabrotica balteata (Corn Root Worm):
A 24-well microtiter plate (MTP) with artificial diet was treated with test solutions at an application rate of 200 ppm (concentration in well 18 ppm) by pipetting. After drying, the MTP's were infested with larvae (L2) (6-10 per well). After an incubation period of 5 days, samples were checked for larval mortality, and growth regulation.
The following compounds gave at least 80% control of Diabrotica balteata: A5, A6, A7, A14, A15, A18, A24, A35, A53, A55, A70, A71, A75, A79, A84, A85, A88, A92, A93, A95, A96, A97, A98, A99, A100, A101, A102, A103, and A104.

Myzus persicae (Green Peach Aphid):
Each well of a 24-well microtiter plate is filled with 0.6 ml 30% sucrose solution, containing 12.5 ppm of the test compounds. The wells are covered with streched parafilm and infested with a mixed population of Myzus persicae. After an incubation period of 6 days, samples are checked for mortality (feeding activity).
The following compounds gave at least 80% control of Myzus persicae: A4, A6, A10, A11, A15, A19, A20, A24, A27, A29, A33, A34, A36, A37, A39, A40, A41, A42, A43, A44, A45, A46, A47, A48, A49, A55, A60, and A82.

Tetranychus urticae (Two-Spotted Spider Mite):
Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.
The following compounds gave at least 80% control of Tetranychus urticae: A6, A11, A15, A19, A20, A22, A26, A35, A58, and A64.

Compound Nos. A1, A12, A17, A21, A23, A30, A51, A52, A54, A56, A57, A61, A62, A63, A66, A67, A68, A72, A81, A83, and A91 were tested using the same protocols and showed no or little effect on mortality, feeding behavior, or growth regulation under the test conditions.

The invention claimed is:
1. A compound of formula (I):

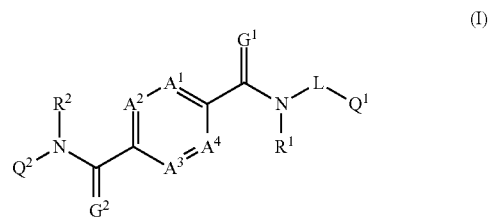

wherein
$A^1$, $A^2$, $A^3$ and $A^4$ are independently of each other C—H, C—$R^3$;
$G^1$ and $G^2$ are oxygen;
$R^1$ is hydrogen, $C_1$-$C_8$alkyl, $C_1$-$C_8$alkylcarbonyl-, or $C_1$-$C_8$alkoxycarbonyl-;
$R^2$ is hydrogen, $C_1$-$C_8$alkyl, $C_1$-$C_8$alkylcarbonyl-, or $C_1$-$C_8$alkoxycarbonyl-;
each $R^3$ is independently halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkylcarbonyl-, or $C_1$-$C_8$alkoxycarbonyl-;
L is a single bond, or $C_1$-$C_6$alkylene;
$Q^1$ is $C_1$-$C_8$alkyl or $C_1$-$C_8$alkyl substituted by one to five $R^4$; or
$Q^1$ is $C_3$-$C_{10}$cycloalkyl or $C_3$-$C_{10}$cycloalkyl substituted by one to five $R^5$, or $C_3$-$C_{10}$cycloalkenyl or $C_3$-$C_{10}$cycloalkenyl substituted by one to five $R^5$, or
$Q^1$ is aryl or aryl substituted by one to five $R^6$, heterocyclyl or heterocyclyl substituted by one to five $R^6$, aryloxy or aryloxy substituted by one to five $R^6$, or heterocyclyloxy or heterocyclyloxy substituted by one to five $R^6$;
each $R^4$ is independently halogen, hydroxy, $C_1$-$C_8$alkoxy, N—$C_1$-$C_8$alkylamino-, N,N-di-($C_1$-$C_8$alkyl)amino-, N—$C_1$-$C_8$alkylcarbonylamino-, or (HOSO$_2$)S—;
each $R^5$ is independently halogen, hydroxy, $C_1$-$C_8$alkyl, or $C_1$-$C_8$alkoxycarbonyl-;
each $R^6$ is independently halogen, cyano, nitro, $C_1$-$C_8$alkyl, $C_1$-$C_8$haloalkyl, $C_1$-$C_8$alkoxy, $C_1$-$C_8$haloalkoxy, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, N—$C_1$-$C_8$alkylamino-, N,N-di-($C_1$-$C_8$alkyl)amino-, N—$C_1$-$C_8$alkylcarbonylamino-, aryl or aryl substituted by one to five $R^7$, heterocyclyl or heterocyclyl substituted by one to five $R^7$, aryl-$C_1$-$C_4$alkyl- or aryl-$C_1$-$C_4$alkyl- wherein the aryl moitey is substituted by one to five $R^7$, heterocyclyl-$C_1$-$C_4$alkyl- or heterocyclyl-$C_1$-$C_4$alkyl- wherein the heterocyclyl moitiey is substituted by one to five $R^7$, aryloxy or aryloxy substituted by one to five $R^7$, or heterocyclyloxy or heterocyclyloxy substituted by one to five $R^7$;

each $R^7$ is independently halogen, cyano, nitro, $C_1$-$C_8$alkyl, $C_1$-$C_8$haloalkyl, $C_1$-$C_8$alkoxy, or $C_1$-$C_8$haloalkoxy; and $Q^2$ is a moiety of formula (II)

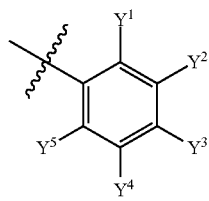

(II)

wherein $Y^1$ and $Y^5$ are independently of each other halogen, cyano, $C_1$-$C_8$alkyl, $C_1$-$C_8$haloalkyl, $C_1$-$C_4$alkoxy-$C_1$-$C_4$-alkyl-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

$Y^3$ is $C_2$-$C_8$perfluoroalkyl, $Y^2$ and $Y^4$ are independently of each other hydrogen, halogen, or $C_1$-$C_8$alkyl.

2. The compound according to claim 1 wherein $R^1$ is hydrogen, methyl, ethyl, methylcarbonyl-, or methoxycarbonyl-.

3. The compound according to claim 1 wherein $R^2$ is hydrogen, methyl, ethyl, methylcarbonyl-, or methoxycarbonyl-.

4. The compound according to claim 1 wherein each $R^3$ is independently halogen, cyano, $C_1$-$C_8$alkyl, or $C_1$-$C_8$haloalkyl.

5. The compound according to claim 1 wherein L is a single bond, —$CH_2$—, —$CH_2$—$CH_2$—, —$CH(CH_3)$—, or —$CH_2$—$CH_2$—$CH_2$—.

6. A composition comprising a compound of formula (I) as defined in claim 1.

7. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1, with the proviso that the formula does not include compound A1, A12, A17, A21, A23, A30, A51, A52, A54, A56, A57, A61, A62, A63, A66, A67, A68, A72, A81, A83, and A91.

* * * * *